(12) United States Patent
Nwoko et al.

(10) Patent No.: US 6,362,361 B1
(45) Date of Patent: Mar. 26, 2002

(54) PEROXYKETALS DERIVED FROM CYCLIC BETA-KETO ESTERS

(75) Inventors: Delphine Nwoko, Longview, TX (US); Michael Wells, Boalsburg, PA (US); Lawrence Bock, Longview, TX (US)

(73) Assignee: Crompton Corporation, Middlebury, CT (US)

( * ) Notice: Subject to any disclaimer, the term of this patent is extended or adjusted under 35 U.S.C. 154(b) by 0 days.

(21) Appl. No.: 09/887,386

(22) Filed: Jun. 22, 2001

(51) Int. Cl.[7] ............................................... C07C 69/74
(52) U.S. Cl. ...................................................... 560/122
(58) Field of Search ................................. 560/116, 121, 560/122, 126; 568/558, 563; 252/182.28, 183.13

(56) References Cited

U.S. PATENT DOCUMENTS

| 2,455,569 A | 12/1948 | Dickey |
| 2,650,913 A | 9/1953 | Boyd |
| 2,656,334 A | 10/1953 | D'Alelio |
| 2,692,260 A | 10/1954 | D'Alelio |
| 3,296,184 A | 1/1967 | Portolani et al. |
| 3,344,125 A | 9/1967 | Gerritsen et al. |
| 3,433,825 A | 3/1969 | Maltha et al. |
| 3,763,275 A | 10/1973 | Groepper et al. |
| 4,032,596 A | 6/1977 | Uffner et al. |
| 4,052,543 A | 10/1977 | McKellin et al. |
| 4,328,360 A | 5/1982 | McKellin et al. |
| 4,365,086 A | 12/1982 | McKellin et al. |

FOREIGN PATENT DOCUMENTS

| DE | 2438675 A1 * | 3/1975 |
| GB | 1047830 | 6/1964 |

* cited by examiner

Primary Examiner—Gary Geist
Assistant Examiner—Paul A. Zucker
(74) Attorney, Agent, or Firm—Daniel Reitenbach

(57) ABSTRACT

This invention relates to peroxyketals derived from cyclic β-keto esters and use of the same in the curing of resins, such as unsaturated polyester resins. The new peroxyketals were synthesized via an acid catalyzed reaction of cyclic β-keto esters with aliphatic hydroperoxides.

36 Claims, No Drawings

PEROXYKETALS DERIVED FROM CYCLIC BETA-KETO ESTERS

BACKGROUND OF THE INVENTION

1. Field of the Invention

The present invention relates to peroxyketals; more specifically to a class of peroxyketals derived from cyclic β-keto esters. Among other things, the peroxyketals of the present invention provide for improved curing of various resins, such as polyesters, than heretofore obtainable. In another aspect, the invention relates to the curing of resins using such peroxyketals.

2. Description of the Prior Art

Organic peroxides have multifarious commercial applications, many of which predominate in the polymer industry. There, organic peroxides are used inter alia to cure various resins, such as unsaturated polyesters, and epoxy vinyl esters; and to crosslink homo- and co-polymers of ethylene and various rubbers. They are also used to polymerize vinyl monomers such as vinyl chloride, styrene, etc.

It is necessary for organic peroxides having uses in commercial and industrial applications in the polymerization and copolymerization of polyesters to be readily reactable and of low cost. The more cost effective the organic peroxide the more applicable the material will be to the industry. One means of decreasing the cost associated with such a material is by decreasing the resin cure time, thus enabling more polymerizations to be conducted over a given period of time.

Peroxyketals have been the subject of several disclosures in the prior art. For example, U.S. Pat. No. 2,455,569 first disclosed peroxyketals obtained from the reaction of tertiary organic hydroperoxides and carbonyl-containing compounds.

2,2-Bis(tertiary butylperoxy)butane is disclosed in U.S. Pat. No. 2,650,913 to be a catalyst for the polymerization of ethylene.

U.S. Pat. Nos. 2,656,334 and 2,692,260 report the use of 2,2-di-(tertiarybutylperoxy)butane as one part of a two component catalyst system useful for polymerization of vinyl compounds.

A series of patents (Great Britain 1,047,830; U.S. Pat. Nos. 4,052,543; 4,328,360; 4,365,086) disclose compounds such as n-butyl 4,4-bis(t-butylperoxy)valerate and ethyl 3,3-bis(t-butylperoxy)butyrate.

U.S. Pat. No. 3,296,184 discloses a series of peroxyketals used to vulcanize polymers and copolymers.

U.S. Pat. No. 3,344,125 discloses a series of substituted cyclohexane peroxyketals.

Esters of 4,4-ditert-butylperoxy pentanoic acid are reported in U.S. Pat. No. 3,433,825 as useful for the crosslinking of copolymers of ethylene and monomers containing terminal vinyl groups.

U.S. Pat. No. 3,763,275 discloses the polymerization of ethylenically unsaturated monomers and the curing of unsaturated polyester resins and elastomers using β-substituted diperoxyketals.

U.S. Pat. No. 4,032,596 reports the use of quaternary ammonium salts as cure accelerators for unsaturated polyester resins containing peroxyketal initiators.

Notwithstanding the teachings of the peroxide materials reported by these printed publications, the prior art is deficient with respect to improved gel times and amelioration of exothermic behavior. Clearly there still remains a need for providing new and improved organic peroxides for use in the polymerization and copolymerization of polyesters. Moreover, there is a need for providing a cost effective organic peroxide which is both thermally stable and which increases the speed with which it polymerizes or copolymerizes a material being acted upon. Such an organic peroxide preferably decreases the gel time of resins which it acts upon and may preferably decrease the exothermic temperature of the reaction as a whole.

SUMMARY OF THE INVENTION

The present invention is directed to a class of peroxyketals derived from cyclic β-keto esters and the use of such peroxyketals in the curing of unsaturated polyester resins. Particularly the present invention provides a peroxyketal comprising the general structure:

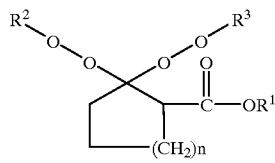

wherein;
  $R^1$ is $C_1$–$C_{10}$ alkyl, cycloalkyl, alkaryl, or aryl which may be unsubstituted or substituted with one or more halogen or hydroxy;
  $R^2$ and $R^3$ are each independently $C_1$–$C_{10}$ alkyl, cycloalkyl, or aralkyl; and
  n is 1, 2 or 3.

As will be made clearer herein, the peroxyketals of the instant invention unexpectedly manifest significantly reduced gel times as compared to the organic peroxides of the prior art. Reduced gel time in this regard will be appreciated as enabling an increased speed of polymerization or copolymerization.

In accordance with another aspect of the present invention, a method of curing a resin is provided wherein a curable cross-linkable resin is contacted with a cure-effective amount of a peroxyketal having the structure:

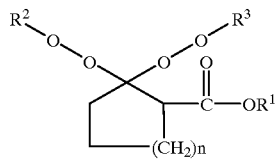

wherein;
  $R^1$ is $C_1$–$C_{10}$ alkyl, cycloalkyl, alkaryl, or aryl which may be unsubstituted or substituted with one or more halogen or hydroxy;
  $R^2$ and $R^3$ are each independently $C_1$–$C_{10}$ alkyl, cycloalkyl, or aralkyl; and
  n is 1, 2 or 3.

Another benefit provided by the practice of the present invention is a lessening of the exothermic nature of the underlying polymerization reactions which may be found useful in some applications, compared to the prior art. Beneficially, when the curing reaction generates less heat overall, there is a lessening of the development of internal stresses in the cured resin. This in turn will lessen the likelihood of the cured part developing cracks. Product cracking occurs when the heat of exotherm cannot be dissipated satisfactorily, typically during the heating or cooling processes. Product cracking in polymerized and copolymerized reactions potentially results in a total loss of product.

DETAILED DESCRIPTION OF THE INVENTION

As stated above, the present invention is directed to a class of peroxyketals derived from β-keto esters. The peroxyketals of the present invention comprising the general structure:

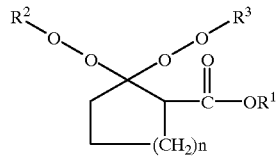

wherein;
  $R^1$ is $C_1$–$C_{10}$ alkyl, cycloalkyl, alkaryl, or aryl which may be unsubstituted or substituted with one or more halogen or hydroxy;
  $R^2$ and $R^3$ are each independently $C_1$–$C_{10}$ alkyl, cycloalkyl, or aralkyl; and
  n is 1, 2 or 3.

The substituents referred to are defined herein as follows:
  The $C_1$–$C_{10}$ alkyl group may be either normal or branched; preferably $R^1$ is of the lower alkyl groups in the range from $C_1$–$C_5$, such as methyl, ethyl, propyl, isopropyl, butyl, isobutyl, t-butyl, t-amyl, pentyl, and the like.
  The cycloalkyl group is $C_5$–$C_7$, preferably cyclohexane ($C_6$).
  Each aryl group consists of one or more aromatic rings of $C_6$–$C_{10}$, including phenyl ($C_6$) and α- and β-naphthyl ($C_{10}$). Each aryl group may be unsubstituted or substituted with one or more halogen or hydroxy groups.
  Each alkaryl group contains up to twenty carbon atoms where each aryl group is $C_6$–$C_{10}$ substituted with one or more $C_1$–$C_{10}$ alkyl groups. Preferably the aryl group is phenyl ($C_6$). Each alkyl group is in the normal or branched configuration and is preferably $C_1$–$C_3$.
  Each aralkyl group contains up to twenty carbon atoms where each alkyl group is $C_1$–$C_{10}$ and is substituted with one or more aryl groups; each alkyl group is in the normal or branched configuration and is preferably $C_1$–$C_4$; $C_3$ being most preferred. Each aryl group is $C_6$–$C_{10}$. In addition, each aryl group may be unsubstituted or substituted with one or more alkyl groups of $C_1$–$C_3$; a preferred aryl is phenyl ($C_6$). A preferred aralkyl is cumyl.

In a first preferred embodiment of the invention, $R^1$ is methyl; in a second preferred embodiment, $R^1$ is ethyl. Preferably, $R^2$ and $R^3$ are each independently $C_3$–$C_8$ alkyls, more preferably they are each independently $C_3$–$C_6$ alkyls, such as propyl, isopropyl, butyl, isobutyl, t-butyl, t-amyl, pentyl, hexyl, and the like. In a preferred practice, $R^2$ and $R^3$ are each independently branched alkyls, including more preferably t-butyl or t-amyl. In a most preferred embodiment, $R^2$ and $R^3$ are the same substituents, e.g. $R^2$ and $R^3$ each are t-butyl or t-amyl. In a preferred practice, n is 1 or 2. In yet another preferred embodiment, $R^2$ and $R^3$ are both aralkyls. Preferably the aralkyls are cumyl groups.

Specific examples of peroxyketals contemplated by the present invention include, but are not limited to, ethyl 2,2-di(tertiary-butylperoxy)-1-cyclohexane carboxylate, ethyl 2,2-di(tertiary-butylperoxy)-1-cyclopentane carboxylate, ethyl 2,2-di(tertiary-amylperoxy)-1-cyclohexane carboxylate, ethyl 2,2-di(tertiary-amylperoxy)-1-cyclopentane carboxylate, methyl 2,2-di(tertiary-butylperoxy)-1-cyclopentane carboxylate, methyl 2,2-di(tertiary-butylperoxy)-1-cycloheptane carboxylate, and the like, for example.

In another aspect, the present invention provides a method of curing a resin comprising contacting a curable or cross-linkable resin with a cure-effective amount of a peroxyketal having the structure:

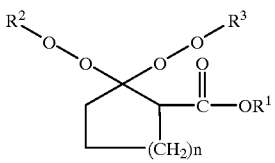

wherein;
  $R^1$ is $C_1$–$C_{10}$ alkyl, cycloalkyl, alkaryl, or aryl which may be unsubstituted or substituted with one or more halogen or hydroxy;
  $R^2$ and $R^3$ are each independently $C_1$–$C_{10}$ alkyl, cycloalkyl, or aralkyl; and
  n is 1, 2 or 3.

Without limitation, curable or cross-linkable resins contemplated by the method of the invention include, for example, unsaturated polyesters including orthophthalic resins, isophthalic resins, dicyclopentadiene resins; epoxy vinyl ester resins including epoxy novolac-based vinyl ester resins; elastomers including ethylene-propylene copolymers; thermoplastics such as polyethylene; and rubbers such as silicone rubber and styrene-butadiene rubber; or the like.

In the practice of this invention the peroxyketals described aforesaid may be utilized in cure effective amounts. While not being limited to particular quantities, a cure effective amount is determinable relative to the subject resin. Exemplary cure effective amounts are within the range of about 0.5 to about 3.0 peroxyketal parts per hundred parts of resin (phr); preferably about 1.0 to about 1.5 phr.

The peroxyketals of the present invention may be prepared as physical mixtures in the form of liquids, granules, powders or flakes. A physical mixture in accordance with the present invention may be prepared by mixing a peroxyketal with the desired amount of solvent to retain reactivity and usefulness in polymerizations and copolymerizations.

Suitable organic solvents include those normally employed for such peroxides, such as esters of phthalic acid, and aliphatic and aromatic hydrocarbons and mixtures of such hydrocarbons, examples of which include hexane, mineral oil, benzene, toluene, xylene and (iso)paraffins. Other suitable solvents will be familiar to one of ordinary skill in the art.

EXAMPLES

Unless noted otherwise, the following general procedures were employed to synthesize the peroxyketals of the present invention. The peroxyketals were prepared via a reaction of a composition comprising a cycloalkanone with a tertiary alkyl hydroperoxide in the presence of an acid and recovering the product by purifying the organic layer of the resulting composition.

The peroxyketals of the present invention were synthesized from a cycloalkanone and a tertiary hydroperoxide according to the following reaction scheme:

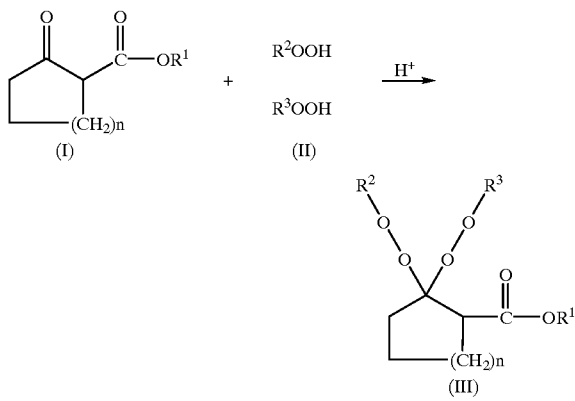

Wherein n, $R^1$, $R^2$ and $R^3$ are as hereinbefore defined.

Generally, the preparation of the present inventive peroxyketal (III) involves the addition of a hydroperoxide (II) to a cyclic β-keto ester (I) at room temperature in a three necked 250-mL round bottomed flask equipped with a thermometer and mechanical stirrer. The solution is then cooled to a temperature of approximately −10° C. via a dry ice-acetone bath and reacted with an acid such as sulfuric acid. The acid is added dropwise to the solution with a temperature at −10° C. Preferably the sulfuric acid is of the 70–78% by weight grade sulfuric acid. Upon completion of the acid addition, the solution is then allowed to warm to a temperature above 0° C., preferably reaching approximately 5° C. where it is then maintained in an ice-water bath for approximately three hours with a mechanical stirring device.

Once the reaction is complete, the produced solution is then transferred to a separatory funnel and the lower acidic aqueous layer is separated and discarded. The organic layer is washed with a washing solution until the pH pf the washing solution is 4.5 or greater. Preferably the washing solution is comprised of saturated NaCl or a saturated solution of NaCl followed by a 2% NaOH solution to bring the pH to a desired level. Desired pH levels are preferably between approximately 4.5 to approximately 7.0.

The organic layer is then dried over $MgSO_4$ and filtered through a Buchner funnel to give the resulting peroxide. Further purification of the product can be carried out by crystallization or column chromatography using silica gel. Gas Chromatography (GC) may further be used to both analyze the product for purity and/or determine the 10 hr half-life temperature.

By way of exemplification only, suitable β-keto esters for the synthesis include cycloalkanones such as, for example, ethyl 2-oxo-1-cyclohexanecarboxylate, ethyl 2-oxo-1-cyclopentane carboxylate, methyl 2-oxo-1-cycloheptane carboxylate and methyl 2-oxo-1-cyclopentanecarboxylate. Other suitable β-keto esters will be familiar to one of ordinary skill in the art. Typically the ketone will be within the range of 90%–100% purity, preferably 95% purity.

Some hydroperoxides useful in this synthesis include tertiary hydroperoxides such as, for example, TBHP (tertiary butyl hydroperoxide), TAHP (tertiary amyl hydroperoxide), and CHP (cumyl hydroperoxide). Other suitable hydroperoxides will be familiar to one of ordinary skill in the art. Typically the hydroperoxide will be within the range of 85% to 100% purity, preferably above 90% purity.

Although the effect of water present during the reaction was never determined, the least amount of water was always the preferred reaction.

The sulfuric acid to β-keto ester mole ratio seemed to cause a large difference in the yields in that more acid resulted in less conversion of the keto ester to product. Thus it is preferable to utilize as little acid as is effective to catalyze the reaction of the β-keto ester and the hydroperoxide. Typically the molar ratio range of acid to β-keto ester is about 0.5 to about 1.5, preferably 1.0-1.2. Other suitable acids will be familiar to one of ordinary skill in the art.

Optionally a base is utilized in the purification of some products but may not be preferable in the purification of others. The use of base to remove excess hydroperoxide from all products is not employed as this appears to hydrolyze some products, thereby reducing the yields. In some reactions, contacting the product with basic solutions as dilute as 2% NaOH during the washings causes some products to become slightly exothermic and turn pink. Base may preferably be utilized to remove residual TAHP in reactions utilizing such, as which will be seen in Example 5. Other suitable bases will be familiar to one of ordinary skill in the art.

Example 1

Sample Analysis by Gas Chromatopranhy

Gas Chromatography (GC) optimally analyzes all peroxyketals prepared for percent purity. The GC methods used to analyze the purity of products are conventional in the art. The GC instrument was equipped with a flame ionization detector (FID). The column was a methyl silicone gum column such as Hewlett Packard HP-1 of dimensions 5 m×0.53 mm wherein the film thickness was 2.65 μm.

The injector port of the GC was heated and maintained at a temperature suitable for analysis (120° C.). The oven was also heated and maintained at a temperature suitable for analysis (40° C.). The detector temperature was 350° C. The sample was then injected using a GC syringe wherein the internal standard is reagent grade nonane. The solvent is preferably petroleum ether. Thus the oven was held for 7 minutes at 40° C. and then ramped to 120° C. at 20° C./minute, held for 3 minutes, then ramped to 175° C. at 20° C./minute and held for 5 minutes.

Example 2

Preparation of Ethyl 2,2-di(tertiary butylperoxy)-1-cyclohexanecarboxylate

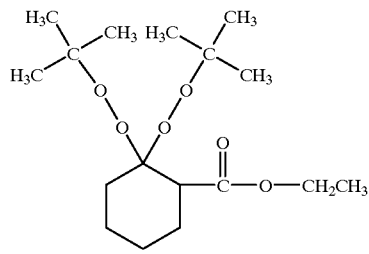

Ethyl 2,2-di(tertiary-butylperoxy)-1-cyclohexanecarboxylate was prepared by the addition of 92.28% TBHP (tertiary butyl hydroperoxide) (24.41 g, 0.2500 moles) to 95% ethyl 2-oxo-1-cyclohexanecarboxylate (17.92 g, 0.1000 moles) at room temperature in a three necked 250-mL round bottomed flask equipped with a thermometer and mechanical stirrer. The solution was then cooled to −10° C. via a dry ice-acetone bath and 78% sulfuric acid (15.09 g, 0.1200 moles) added dropwise to the solution with temperature at −10° C. Upon completion of the addition of sulfuric acid, the solution was allowed to reach 5° C. where it was maintained by an ice-water bath for three hours with mechanical stirring. The reaction was transferred to a separatory funnel and the lower acidic aqueous layer separated and discarded. The organic layer was then washed with saturated NaCl solution until the aqueous washings had a pH of 4.5 or greater. The organic layer was then dried over MgSO$_4$ and filtered through a Buchner funnel to give a resulting peroxide (24.92 g, 74.92%). The resulting peroxide crystallized and was subsequently re-crystallized with hexanes, analyzed for purity by Gas Chromatography, as presented in Example 1, (95% by area) and it's 10 hr half life temperature was determined to be 93.31° C. by G.C.: m.p. 36–38°; $^{13}$C NMR (75 MHz, CDCl$_3$) δ 171.8 (C=O), 106.1 (O—C—O, cyclic), 79.0 (C(CH$_3$)$_3$), 78.9 (C(CH$_3$)$_3$, 59.5 (CH$_2$CH$_3$), 44.3 (CH, Cyclic), 27.6 (CH$_2$, cyclic), 26.3 ((CH$_3$)$_3$), 26.2 ((CH$_3$)$_3$), 2.17 (CH$_2$, cyclic), 21.4 (CH$_2$, cyclic), 13.8 (CH$_3$CH$_2$—O); IR (NaCl, CHCl$_3$) ν 1735, 1370, 1200, 880 Cm$^{-1}$; Analysis calculated for C$_{17}$H$_{32}$O$_6$: C, 61.42; H, 9.70; O, 28.88; found: C, 61.05; H, 9.82: O, 28.22.

Example 3

Preparation of Ethyl 2,2-di(tertiary butylperoxy)-1-cylopentanecarboxylate

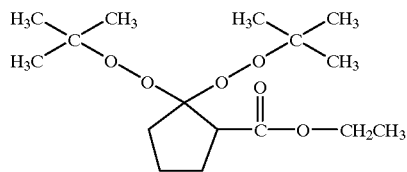

Ethyl 2,2-di(tertiary-butylperoxy)-1-cyclopentanecarboxylate was prepared by the addition of 92.28% TBHP (tertiary butyl hydroperoxide) (24.41 g, 0.2500 moles) to 95% ethyl 2-oxo-cyclopentanecarboxylate (16.44 g, 0.1000 mol) in a three necked 250-mL round bottomed flask equipped with a thermometer and mechanical stirrer at room temperature. The solution was cooled to −10° C. via a dry ice-acetone bath and 70% sulfuric acid (16.81 g, 0.1200 mol) was added dropwise to the solution with temperature at −10° C. Upon completion of the addition of sulfuric acid, the solution was allowed to reach 5° C. where it was maintained by an ice-water bath for three hours with mechanical stirring. The reaction was transferred to a separatory funnel and the lower acidic aqueous layer separated and discarded. The organic layer was then washed with saturated NaCl solution until the aqueous washings had a pH of 4.5 or greater. The organic layer was then dried over MgSO$_4$, filtered through a Buchner funnel and analyzed for purity by gas chromatography (87.98% by area). Purification by chromatography (silica gel, 90:10 petroleum ether/diethyl ether) afforded a liquid product: $^{13}$C NMR (75 MHz, CDCl$_3$) δ 171.8 (C=O), 116.8 (O—C—O, cyclic), 79.6 (C(CH$_3$)$_3$, 79.2 (C(CH$_3$)$_3$, 59.8 (O—CH$_2$CH$_3$), 49.5 (CH, cyclic), 32.9 (CH$_2$, cyclic), 27.7 (CH$_2$, cyclic) 26.2 ((CH$_3$)$_3$), 26.1 ((CH$_3$)$_3$), 22.1 (CH$_2$, cyclic) 13.8 (CH$_2$CH$_3$); IR (neat) ν 1735, 1364, 1198, 878 cm$^{-1}$; Analysis calculated for C$_{16}$H$_{30}$O$_6$; C, 60.36, H, 9.50; O, 30.15; found: C, 60.36; H, 9.58; O, 29.11.

Example 4

Preparation of Ethyl 2,2-di(tertiary amylperoxy)-1-cyclohexanecarboxylate

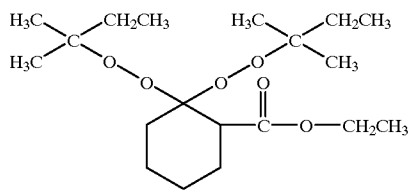

Ethyl 2,2-di(tertiary-amylperoxy)-1-cyclohexanecarboxylate was prepared by the addition of 92.64% TAHP (tertiary amyl hydroperoxide) (42.16 g, 0.3750 mol) to 95% ethyl 2-oxo-1-cyclohexanecarboxylate (17.92 g, 0.1000 mol) at room temperature in a three necked 250-mL round bottomed flask equipped with a thermometer and mechanical stirrer. The solution was cooled to −10° C. via a dry ice-acetone bath and 78% sulfuric acid (15.09, 0.1200 mol) was added dropwise to the solution with the temperature at −10° C. Upon completion of the addition of sulfuric acid, the solution was allowed to reach 5° C. where it was maintained by an ice-water bath for three hours with mechanical stirring. The reaction was transferred to a separatory funnel and the lower acidic aqueous layer separated and discarded. The organic layer was then washed with saturated NaCl solution until the aqueous washings had a pH of 4.5 or greater. The organic layer was then dried over MgSO$_4$, filtered through a Buchner funnel and analyzed for purity by gas chromatography (53% by area). Purification by chromatography (silica gel, 95:5 petroleum ether/diethyl ether) afforded a liquid product: $^{13}$C NMR (75 MHz, CDCl$_3$) δ 171.8 (C=O), 106.0 (O—C—O, cyclic), 81.1 (C—(CH$_3$)$_2$CH$_2$), 81.0 (C(CH$_3$)$_2$CH$_2$), 59.6 (O—CH$_2$CH$_3$), 44.0 (CH, cyclic), 3.16 (CH$_3$—CH$_2$—C), 31.5 (CH$_3$CH$_2$—C), 26.0 (CH$_2$, cyclic), 23.6 (C(CH$_3$)$_2$, (2x)), 21.8 (CH$_2$, cyclic), 22.0 (CH$_2$, cyclic), 13.8 ((O—CH$_2$CH$_3$) (2X)), 8.0 ((CCH$_2$CH$_3$) (2x)); IR (neat) ν 1736, 1364, 1220, 872 cm$^{-1}$.

Example 5

Preparation of Ethyl 2,2-di(tertiary amylperoxy)-1-cyclopentanecarboxylate

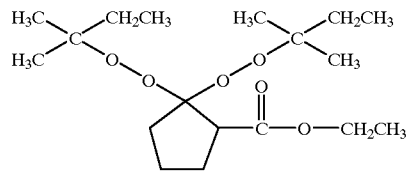

Ethyl 2,2-di(tertiary-amylperoxy)-1-cyclopentanecarboxylate was prepared by the addition of 92.64% TAHP (tertiary amyl hydroperoxide) (42.16 g, 0.3750 mol) to 95% ethyl 2-oxo-1-cyclopentanecarboxylate (16.44 g, 0.1000 mol) at room temperature in a three necked 250-mL round bottomed flask equipped with a thermometer and mechanical stirrer. The solution was then cooled via a dry ice-acetone bath to −10° C. and 78% sulfuric acid (15.09 g, 0.1200 mol) added dropwise to the solution with temperature at −10° C. Upon completion of the addition of sulfuric acid, the solution was allowed to reach 5° C. where it was maintained by an ice-water bath for three hours with mechanical stirring. The reaction was transferred to a separatory funnel and the lower acidic aqueous layer separated and discarded. The organic layer was then dissolved in petroleum ether and washed with saturated NaCl solution followed by 2% NaOH solution to bring aqueous washings to a pH of 4.5 to 7.0. The organic layer was then dried over $MgSO_4$, filtered, stripped to remove the organic solvent and then analyzed for purity by gas chromatography (66% by area). Purification by chromatography (silica gel, petroleum ether) afforded a liquid product: $^{13}C$ NMR (75 MHz, $CDCl_3$) δ 171.9 (C=O), 116.8 (O—C—O, cyclic), 81.8 ($\underline{C}(CH_3)_2$), 81.4 ($\underline{C}(CH_3)_2$, 59.9 (O—$\underline{C}H_2CH_3$), 49.5 (CH, cyclic), 33.0 ($CH_2$, cyclic), 31.6 ($C\underline{C}H_2CH_3$, (2X)), 27.9 ($CH_2$, cyclic), 23.8 ($C(\underline{C}H_3)_2$, (2x)), 22.2 ($CH_2$, cyclic), 13.8 (O—$CH_2$ $\underline{C}H_3$), 8.0 ($C\underline{C}H_2CH_3$, (2x)); IR (neat) v 1736, 1366, 1202, 875 $cm^{-1}$; Analysis calculated for $C_{18}H_{34}O_6$: C, 62.40; H, 9.89; O, 27.71; found: C, 62.40: H, 10.14; O, 26.93.

Example 6

Preparation of Methyl 2,2-di(tertiary butylperoxy)-1-cyclopentanecarboxylate

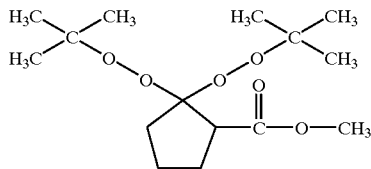

Methyl 2,2-di(tertiary-butylperoxy)-1-cyclopentanecarboxylate was prepared by the addition of 92.28% TBHP (tertiary butyl hydroperoxide) (36.62 g, 0.3750 mol) to 97% methyl 2-oxo-1-cyclopentanecarboxylate (14.65 g, 0.1000 mol) at room temperature in a three necked 250-mL round bottomed flask equipped with a thermometer and mechanical stirrer. The solution was then cooled via a dry ice-acetone bath to −5° C. and 78% sulfuric acid (15.09 g, 0.1200 mol) was added dropwise to the solution with temperature at −5° C. Upon completion of the addition of sulfuric acid, the solution was allowed to reach 5° C. where it was maintained by an ice-water bath for three hours with mechanical stirring. The reaction was transferred to a separatory funnel and the lower acidic aqueous layer separated and discarded. The organic layer was then washed with saturated NaCl solution until the aqueous washings had a pH of 4.0 to 4.5. The organic layer was then dried over $MgSO_4$, filtered through a Buchner funnel and analyzed for purity by gas chromatography (88% by area): $^1H$ NMR (300 MHz, $CDCl_3$) δ 3.7 (s, 3H, $CH_3$), 3.3–3.4 (m, 1H, cyclic H), 1.9–2.2 (m, 6H, cyclic H), 1.3 (s, 9H, $CH_3$), 1.2 (s, 9H, $CH_3$); $^{13}C$ NMR (75 MHz, $CDCl_3$) δ 172.4 (C=O). 116.9 (O—C—O, cyclic), 79.7 ($\underline{C}CH_3)_3$), 79.4 ($\underline{C}(CH_3)_3$), 51.1 (CH, cyclic), 49.1 ($CH_3$—O), 32.9 ($CH_2$, cyclic), 27.7 ($CH_2$, cyclic), 26.2 ($C(\underline{C}H_3)_3$, (2x)), 22.1 ($CH_2$, cyclic); IR (neat) 1740, 1364, 1198, 878 $cm^{-1}$.

Example 7

Preparation of Methyl 2,2-di(tertiary butylperoxy)-1-cycloheptanecarboxylate

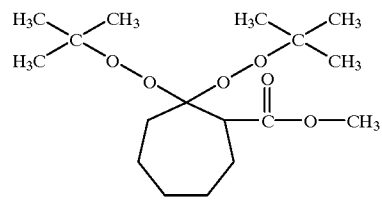

Methyl 2,2-di(tertiary-butylperoxy)-1-cycloheptanecarboxylate was prepared by the addition of 92.28% TBHP (tertiary butyl hydroperoxide) (12.21 g, 0.1250 mol) to 99% methyl 2-oxo-1-cycloheptanecarboxylate (8.600 g, 0.0500 mol) at room temperature in a three necked 125-mL round bottomed flask equipped with a thermometer and mechanical stirrer. The solution was then cooled via a dry ice-acetone bath to −5° C. and 78% sulfuric acid (7.540 g, 0.0600 mol) was added dropwise to the solution with temperature at −5° C. Upon completion of the addition of sulfuric acid, the solution was allowed to reach 5° C. where it was maintained by an ice-water bath for ninety minutes with mechanical stirring. The reaction was transferred to a separatory funnel and the lower acidic aqueous layer separated and discarded. The organic layer was then washed with saturated NaCl solution until the aqueous washings had a pH of 4.5 or greater. The organic layer was then dried over $MgSO_4$, filtered through a Buchner funnel and analyzed by gas chromatography. The purity was found to be 17%. This product was not purified due to low conversion of product.

Example 8

Hot Block Gel Testing

The peroxyketals prepared in examples 2 and 3 were subjected to Hot Block Gel Testing and compared against ethyl 3,3-di-(tertiary butylperoxy) butyrate, representative of a prior art material. The protocol was as follows: A resin sample weighing 50.0±0.10 g was weighed into a 5 oz. paper cup. Cobalt naphthenate (CoNap) (6% solution) was then added (0.10 g) and blended utilizing a spatula. All resin samples were blended consecutively so as to reduce bias errors.

The Hot Block oven was heated to 250° F. Approximately 5 cc of resin was then drawn into an disposable syringe. Once the oven had achieved the proper test temperature, the Hot Block cavity was lubricated using a silicone grease or other release agent. The resin was injected into the Hot Block and the strip chart recorder was set to start.

Table 1 shows the results of the Hot Block Gel tests wherein the temperature was 250° F. and the resin was AROPOL 2036C unsaturated polyester resin (Ashland Chemical). Here it is clearly shown that the products of the present invention outperformed the prior art material. The compounds of the present invention, particularly ethyl 2,2-di(tertiary-butyl peroxy)-1-cyclohexanecarboxylate and ethyl 2,2-di(tertiary-butyl peroxy)-1-cyclopentanecarboxylate expressed a significantly faster gel time and less severe exothermic temperature than an example of the prior art, ethyl 3,3-di-(tertiary butylperoxy) butyrate. The gel time to peak time was improved by as much as 32% by the practice of the invention. By utilizing the peroxyketals of the present invention a decrease in the gel time of nearly 50% was achieved. Furthermore, the peroxyketals of the present invention in Table 1 exhibit a lessening of the peak exotherm temperature of up to about 9%.

TABLE 1

Hot Block Gel Test Results from AROPOL 2036C

| Compound | Perketal (phr) | Gel Time (min.) | Exo. Time (min.) | Peak Exo. (° F.) | Gel to Peak Time (min.) |
|---|---|---|---|---|---|
| Ethyl 2,2-di(tertiary-butyl peroxy)-1-cyclohexanecarboxylate | 1.5 | 1.53 | 1.97 | 334 | 0.44 |
| Ethyl 2,2-di(tertiary-butyl peroxy)-1-cyclopentanecarboxylate | 1.5 | 1.37 | 1.75 | 357 | 0.38 |
| Ethyl 3,3-di-(tertiary butylperoxy)butyrate | 1.5 | 2.72 | 3.28 | 366 | 0.56 |

Example 9

Differential Thermal Analysis (DTA) Data

This example examines the onset temperature effects achieved with the peroxyketals of the present invention. The onset temperature of decomposition of the peroxyketals of the present invention was determined using a differential thermal analyzer. The onset temperature is the point at which an uncontrolled thermal decomposition starts. The onset temperature can be measured by determining the point at which the rate of temperature increase in a sealed cell exceeds a certain pre-determined value. In addition, the onset temperature can be measured by determining the point at which the rate of pressure increase in the sealed cell exceeds a certain predetermined value.

Using a type of Differential Thermal Analyzer (Radex Solo Thermal Analyzer, marketed by Astra Scientific International), with an isothermal hold temperature of 50° C. for 10 minutes and then a temperature increase of 2°/minute to 225° C., the onset temperature was measured for a one gram sample of the peroxyketals of the present invention in a sealed cell.

The onset temperature was measured both by noting the point where the rate of increase ($\Delta T$) of the sample temperature reached 0.2° C./minute and also the point where the rate of increase in pressure ($\Delta P$) of the closed sample cell reached 1.0 psi/minute. $\Delta T$ is the difference between the oven temperature and the sample temperature. $\Delta P$ is the difference between a reference pre-calibrated pressure and the pressure developed in the sealed sample cell.

Table 2 shows the onset temperatures of the compounds of the present invention prepared in accordance with Examples 2 and 3.

TABLE 2

Onset Temperatures

| Compound | Onset Temp. ($\Delta T$) (° C.) | Onset Temp ($\Delta P$) (° C.) |
|---|---|---|
| Ethyl 2,2-di(tertiary butylperoxy)-1-cyclopentanecarboxylate | 99.80 | 107.18 |
| Ethyl 2,2-di(tertiary butyl peroxy)-1-cyclohexanecarboxylate | 97.91 | 104.90 |

Example 10

Differential Scanning Calorimetry (DSC) Data

This example examines the curing of a typical polyester resin using the peroxyketals of the present invention. Compounds of the present invention were examined against a compound of the prior art via Differential Scanning Calorimetry (DSC) wherein data was collected using a Mettler Toledo DSC 821e instrument. The temperature program used was isothermal at 30° C. for 10 min followed by a 5° C./min ramp to 180° C., holding for 1 min. The Pan type was medium Pressure/Viton 120 µL wherein the sample size was 24.000±2 mg. The resin was AROPOL 2036C unsaturated polyester resin (Ashland Chemical).

Table 3 shows a comparison of ethyl 2,2-di(tertiary butylperoxy)-1-cyclohexanecarboxylate and ethyl 2,2-di (tertiary-butyl peroxy)-1-cyclopentanecarboxylate of the present invention, prepared in accordance with Examples 2 and 3 respectively, against ethyl 3,3-di-tertiary butyl peroxybutyrate of the prior art. Here it is clear that the compounds of the present invention initiate the curing of the polyester resin at lower temperatures than the compound of the prior art.

TABLE 3

Onset Temperatures Measured by DSC

| Compound | Perketal (phr) | Onset Temp. (° C.) |
|---|---|---|
| Ethyl 2,2-di(tertiary butyl peroxy)-1-cyclohexanecarboxylate | 1.5 | 113 |
| Ethyl 2,2-di(tertiary-butyl peroxy)-1-cyclopentanecarboxylate | 1.5 | 109 |
| Ethyl-3,3-di-tertiary butyl peroxy butyrate | 1.5 | 128 |

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to exact forms described and illustrated but fall within the scope of the appended claims.

What is claimed is:

1. A cyclic β-ester peroxyketal having the general structure:

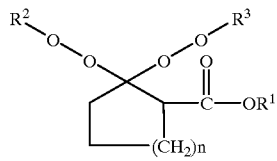

wherein:
  $R^1$ is $C_1$–$C_{10}$ alkyl, cycloalkyl, alkaryl, or aryl which may be unsubstituted or substituted with one or more halogen or hydroxy;
  $R^2$ and $R^3$ are each independently $C_1$–$C_{10}$ alkyl, cycloalkyl, or aralkyl; and
  n is 1, 2 or 3.

2. The peroxyketal of claim 1 wherein $R^1$ is $C_1$–$C_5$ alkyl and $R^2$ and $R^3$ are each independently $C_3$–$C_8$ alkyl.

3. The peroxyketal of claim 2 wherein $R^1$ is methyl.

4. The peroxyketal of claim 2 wherein $R^1$ is ethyl.

5. The peroxyketal of claim 2 wherein $R^2$ and $R^3$ are the same substituent.

6. The peroxyketal of claim 5 wherein $R^2$ and $R^3$ are each t-butyl.

7. The peroxyketal of claim 5 wherein $R^2$ and $R^3$ are each t-amyl.

8. The peroxyketal of claim 5 wherein $R^2$ and $R^3$ are each cumyl groups.

9. The peroxyketal of claim 1 wherein n is 1.

10. The peroxyketal of claim 9 wherein $R^1$ is ethyl and $R^2$ and $R^3$ are each independently t-butyl.

11. The peroxyketal of claim 9 wherein $R^1$ is ethyl and $R^2$ and $R^3$ are each independently t-amyl.

12. The peroxyketal of claim 9 wherein $R^1$ is methyl and $R^2$ and $R^3$ are each independently t-butyl.

13. The peroxyketal of claim 1 wherein n is 2.

14. The peroxyketal of claim 13 wherein $R^1$ is ethyl and $R^2$ and $R^3$ are each independently t-butyl.

15. The peroxyketal of claim 13 wherein $R^1$ is ethyl and $R^2$ and $R^3$ are each independently t-amyl.

16. The peroxyketal of claim 1 wherein n is 3.

17. The peroxyketal of claim 16 wherein $R^1$ is methyl and $R^2$ and $R^3$ are each independently t-butyl.

18. A method for curing a resin comprising:

contacting a curable cross-linkable resin with a cure-effective amount of a peroxyketal having the structure:

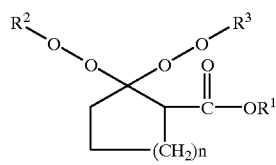

wherein;

$R^1$ is $C_1$–$C_{10}$ alkyl, cycloalkyl, alkaryl, or aryl which may be unsubstituted or substituted with one or more halogen or hydroxy;

$R^2$ and $R^3$ are each independently $C_1$–$C_{10}$ alkyl, cycloalkyl, or aralkyl; and n is 1, 2 or 3.

19. The method of claim 18 wherein $R^1$ is $C_1$–$C_5$ alkyl and $R^2$ and $R^3$ are each independently $C_3C_8$ alkyl.

20. The method of claim 19 wherein $R^1$ is methyl.

21. The method of claim 19 wherein $R^1$ is ethyl.

22. The method of claim 19 wherein $R^2$ and $R^3$ are each independently t-butyl.

23. The method of claim 19 wherein $R^2$ and $R^3$ are each independently t-amyl.

24. The method of claim 18 wherein $R^2$ and $R^3$ are each independently cumyl groups.

25. The method of claim 18 wherein $R^1$ is ethyl and $R^2$ and $R^3$ are each independently t-butyl.

26. The method of claim 25 wherein n is 1.

27. The method of claim 25 wherein n is 2.

28. The method of claim 18 wherein $R^1$ is ethyl and $R^2$ and $R^3$ are each independently t-amyl.

29. The method of claim 28 wherein n is 1.

30. The method of claim 28 wherein n is 2.

31. The method of claim 18 wherein $R^1$ is methyl and $R^2$ and $R^3$ are each independently t-butyl.

32. The method of claim 31 wherein n is 1.

33. The method of claim 31 wherein n is 3.

34. The method of claim 18 wherein the resin is selected from the group consisting of unsaturated polyester resins, epoxy vinyl ester resins, elastomers, thermoplastics, and rubbers.

35. The method of claim 18 wherein the peroxyketal is present in an amount from about 0.5 to about 3.0 phr.

36. The method of claim 35 wherein the peroxyketal is present in an amount from about 1.0 to about 1.5 phr.

* * * * *